United States Patent [19]

Bauer et al.

[11] 4,395,403
[45] Jul. 26, 1983

[54] NOVEL POLYPEPTIDES, PROCESSES FOR THEIR PRODUCTION, PHARMACEUTICAL COMPOSITIONS COMPRISING SAID POLYPEPTIDES AND THEIR USE

[75] Inventors: Wilfried Bauer, Lampenberg; Janos Pless, Basel, both of Switzerland

[73] Assignee: Sandoz Ltd., Basel, Switzerland

[21] Appl. No.: 321,663

[22] Filed: Nov. 16, 1981

Related U.S. Application Data

[63] Continuation-in-part of Ser. No. 208,888, Nov. 21, 1980, abandoned.

[30] Foreign Application Priority Data

Nov. 27, 1979 [CH] Switzerland ...................... 10524/79
Jun. 13, 1980 [CH] Switzerland ........................ 4574/80

[51] Int. Cl.³ ..................... A61K 37/00; C07C 103/52
[52] U.S. Cl. ............................... 424/177; 260/112.5 S
[58] Field of Search .................. 260/112.5 S, 112.5 R; 424/177

[56] References Cited

U.S. PATENT DOCUMENTS

| | | | |
|---|---|---|---|
| 4,225,472 | 9/1980 | Sarantakis | 260/112.5 S |
| 4,282,143 | 8/1981 | Sarantakis | 260/112.5 S |
| 4,310,518 | 1/1982 | Freidinger et al. | 260/112.5 S |

*Primary Examiner*—Delbert R. Phillips
*Attorney, Agent, or Firm*—Gerald D. Sharkin; Robert S. Honor; Thomas O. McGovern

[57] ABSTRACT

Straight-chain and mono-cyclic polypeptides containing the basic sequence $$-\underset{1}{Cys}-\underset{2}{Phe}-\underset{3}{Trp}-\underset{4}{Lys}-\underset{5}{X}-\underset{}{Cys}-/-\underset{6}{Cys}-ol$$

wherein X is an amino acid residue, the residues in the 1- and 6-positions being linked by an —S—S— bridge when the polypeptide is monocyclic, have pharmacological, in particular GH—, gastric- and pancreatic-secretion inhibiting activity.

21 Claims, No Drawings

NOVEL POLYPEPTIDES, PROCESSES FOR THEIR PRODUCTION, PHARMACEUTICAL COMPOSITIONS COMPRISING SAID POLYPEPTIDES AND THEIR USE

The present application is a Continuation-in-Part of our co-pending Application Ser. No. 208,888 filed Nov. 21, 1980, now abandoned.

The present invention provides novel polypeptides, processes for their production, pharmaceutical compositions comprising said polypeptides and their use as pharmaceutically active agents.

More particularly the present invention provides a straight-chain or mono-cyclic polypeptide comprising a hexapeptide residue, said hexapeptide residue having in the 1-position (N-terminal) a cysteine residue, in the 2-position an optionally ring-substituted phenylalanine residue, in the 3-position an optionally benzene-ring-substituted tryptophan residue, in the 4-position an optionally $\epsilon$-N-alkylated lysine residue, in the 5-position an amino acid residue, and in the 6-position (C-terminal) a cysteine or cysteinol residue, the S-atoms of the cysteine residue at the 1-position and the cysteine or cysteinol residue at the 6-position being linked together when the polypeptide is mono-cyclic to form an —S—S—bridge, whereby residues at the 1-, 3-, 5- and 6-positions each independently have the D- or L-configuration and the residues at the 3-, 4- and 5-positions are each independently optionally $\alpha$-N-alkylated, as well as the salt forms and complexes thereof.

Preferred compounds in accordance with the invention are polypeptides of formula I

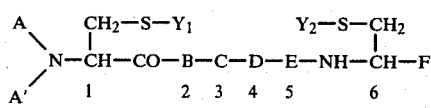

wherein

A is hydrogen, $C_{1-12}$ alkyl, $C_{7-10}$ phenylalkyl or a group of formula RCO—, whereby
  (i) R is hydrogen, $C_{1-11}$ alkyl, phenyl or $C_{7-10}$ phenylalkyl, or
  (ii) RCO— is
    (a) an L- or D-phenylalanine residue optionally ring-substituted by halogen, $NO_2$, $NH_2$, OH, $C_{1-3}$ alkyl and/or $C_{1-3}$ alkoxy
    (b) the residue of a natural $\alpha$-amino acid other than defined under (a) above or of a corresponding D-amino acid, or
    (c) a dipeptide residue in which the individual amino acid residues are the same or different and are selected from those defined under (a) and/or (b) above, the $\alpha$-amino group of amino acid residues (a) and (b) and the N-terminal amino group of dipeptide residues (c) being optionally mono- or di-$C_{1-12}$ alkylated, A' is hydrogen or, when A is $C_{1-12}$ alkyl or $C_{7-10}$ phenylalkyl, also $C_{1-12}$ alkyl or $C_{7-10}$ phenylalkyl B is —Phe— optionally ring-substituted by halogen, $NO_2$, $NH_2$, OH, $C_{1-3}$ alkyl and/or $C_{1-3}$ alkoxy, C is —(L)— or —(D)—Trp— optionally $\alpha$-N-methylated and optionally benzene-ring-substituted by halogen, $NO_2$, $NH_2$, OH, $C_{1-3}$alkyl and/or $C_{1-3}$ alkoxy, D is —Lys— optionally $\alpha$-N-methylated and optionally $\epsilon$—N—$C_{1-3}$ alkylated, E is the residue of a natural $\alpha$-amino acid or of a corresponding D-amino acid, said residue being optionally $\alpha$-N-methylated, F is a group of formula

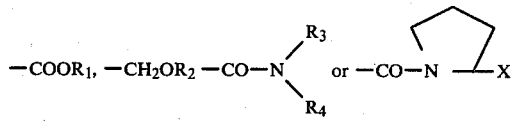

wherein $R_1$ is hydrogen or $C_{1-3}$ alkyl, $R_2$ is hydrogen or the residue of a physiologically acceptable, physiologically hydrolysable ester, $R_3$ is hydrogen, $C_{1-3}$ alkyl, phenyl, benzyl or $C_{9-10}$ phenylalkyl, $R_4$ is hydrogen, $C_{1-3}$ alkyl or, when $R_3$ is hydrogen or methyl, also a group of formula —CH($R_5$)—X wherein $R_5$ is hydrogen, —$(CH_2)_2$—OH or —$(CH_2)_3$—OH, or represents the substituent attaching to the $\alpha$-carbon atom of a natural $\alpha$-amino acid and X is a group of formula —$COOR_1$,

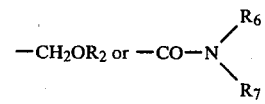

wherein
$R_1$ and $R_2$ have the meanings given above,
$R_6$ is hydrogen or $C_{1-3}$ alkyl and
$R_7$ is hydrogen, $C_{1-3}$ alkyl, phenyl or $C_{7-10}$ phenylalkyl, the group —CH($R_5$)—X having the D- or L-configuration,
$Y_1$ and $Y_2$ are each hydrogen or together represent a direct bond, whereby the residues in the 1- and 6-position each independently have the L- or D-configuration, with the proviso that (i) D- and/or L-cysteine residues are present at the 1- and 6-positions only, and (ii) that when, as the substituent attaching to the $\alpha$-carbon atom of a natural $\alpha$-amino acid, $R_5$ is benzyl (that is, the substituent attaching to the $\alpha$-carbon atom of the amino acid phenylalanine), X is a group of formula

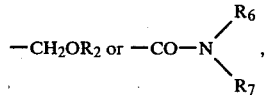

or a group of formula —$COOR_1$, wherein $R_1$ is $C_{1-3}$alkyl, as well as the salt forms and complexes thereof. Throughout the present specification and claims by "halogen" is meant fluorine, chlorine and bromine. In the polypeptides of formula I, the following significances or combinations thereof are preferred:

1. A is $C_{7-10}$ phenylalkyl, especially phenethyl, or a group of formula RCO. Preferably A is a group of formula RCO.

1.1 Preferably R is $C_{1-11}$ alkyl or $C_{7-10}$ phenylalkyl, especially $C_{7-10}$ phenylalkyl, more especially phenethyl, or RCO has the meanings (a), (b) or (c).

1.2. When RCO has the meanings (a), (b) or (c), the $\alpha$-amino group of amino acid residues (a) and (b) and the N-terminal amino group of dipeptide residues (c) is preferably non-alkylated or mono-$C_{1-12}$ alkylated, especially —$C_{1-8}$ alkylated, more especially -methylated. Most preferably the N-terminal is non-alkylated.

1.3 When RCO has the meaning (a) this is preferably (a') an L- or D-phenylalanine or -tyrosine residue optionally mono-N-$C_{1-2}$ alkylated. More preferably (a') is an L- or D-phenylalanine residue or an L- or D-N-($C_{1-8}$-alkyl)-phenylalanine residue. Most preferably (a') is a D-phenylalanine or D-N-($C_{1-8}$ alkyl)-phenylalanine residue, especially a D-phenylalanine or D-(N-methyl)-phenylalanine residue.

1.4 When RCO has the meaning (b) or (C) the defined residue is preferably lipophilic. Preferred residues (b) are thus (b') α-amino acid residues having a hydrocarbon side chain, e.g. leucine and nor-leucine residues, said residues having the L- or D-configuration, and preferred residues (c) are dipeptide residues in which the individual amino acid residues are the same or different and are selected from those defined under (a') and (b') above.

1.5. Most preferably RCO has the meaning (a), especially the meanings (a').

2. B is —Phe—
3. C is —(D)Trp—
4. D is —Lys—, —MeLys— or —Lys(ε—Me)—, especially —Lys—.
5. E is the residue of a natural α-amino acid, especially —Thr—.
6. F is a group of formula

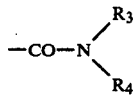

especially a group of formula

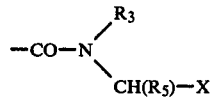

(in which case $R_3$=H or $CH_3$). In the latter case the moiety —CH($R_5$)—X preferably has the L-configuration.

6.1. $R_3$ is preferably hydrogen.
6.2. As the substituent attaching to the α-carbon atom of a natural amino acid (i.e. of formula $H_2N$—CH($R_5$)—COOH) $R_5$ is preferably —$CH_2OH$, —CH($CH_3$)—OH, isobutyl or benzyl, or $R_5$ is ($CH_2$)$_2$—OH or ($CH_2$)$_3OH$. It is especially —$CH_2OH$ or —CH($CH_3$)OH.
6.3. X is preferably a group of fomula

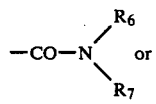

or —$CH_2$—$OR_2$ especially of formula —$CH_2$—$OR_2$ and $R_2$ is preferably hydrogen or has the meaning given under 7 below. Most preferably it is hydrogen.

7. As the residue of a physiologically acceptable, physiologically hydrolysable ester $R_2$ is preferably HCO, $C_{2-12}$ alkylcarbonyl, $C_{8-12}$ phenylalkylcarbonyl or benzoyl.

8. Preferably the residues in the 1- and 6-positions have the L-configuration.

9. Preferably $Y_1$ and $Y_2$ together represent a direct bond. A group of compounds in accordance with the invention are polypeptides of formula I as defined above wherein A is hydrogen, $C_{1-3}$ alkyl, $C_{7-10}$ phenylalkyl or a group of formula RCO—, A' is hydrogen, R is hydrogen, $C_{1-3}$ alkyl, phenyl or $C_{7-10}$ phenylalkyl or RCO is
(a) an L- or D-phenylalanine residue optionally monoring-substituted by halogen, $NO_2$, $NH_2$, OH, $C_{1-3}$ alkyl or $C_{1-3}$ alkoxy, or
(b) the residue of a natural α-amino acid other than defined under (a) above or of a corresponding D-amino acid, the amino group of amino acid residues (a) and (b) being optionally mono-$C_{1-3}$ alkylated, F is a group of formula

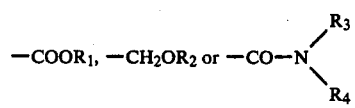

$R_2$ is hydrogen,
$R_3$ is hydrogen or $C_{1-3}$ alkyl,
$R_7$ is hydrogen or $C_{1-3}$ alkyl and
$Y_1$ and $Y_2$ together represent a direct bond, as well as the acid addition salts and complexes thereof.

In a further group of compounds in accordance with the invention: (I) $R_3$ is hydrogen, $C_{1-3}$alkyl or phenyl, particularly hydrogen or $C_{1-3}$alkyl. In a yet further group of compounds in accordance with the invention: (II) when, as the substituent attaching to the α-carbon atom of a natural α-amino acid, $R_5$ is benzyl (that is the substituent attaching to the α-carbon atom of the amino acid phenylalanine, X is a group of formula —$CH_2OR_2$ or —CO—N($R_6$)—$R_7$. In a still further group of compounds in accordance with the invention, the restrictions under (I) and (II) above are made concurrent. In a still further group of compounds in accordance with the invention $R_3$ is hydrogen or methyl and $R_4$ is a group of formula —CH($R_5$)—X.

The polypeptides of the invention may exist in salt form or in the form of complexes thereof. Acid addition salts may be formed with e.g. organic acids, polymeric acids and inorganic acids. Such acid addition salt forms include e.g. the hydrochlorides and acetates. By complexes are to be understood compounds of known type, formed from compounds of formula I on addition of inorganic substances, e.g. inorganic salts or hydroxides such as Ca- and Zn-salts, and/or on addition of polymeric organic substances.

The present invention also provides a process for the production of the compounds according to the invention. These compounds may be produced by methods known in the art of peptide chemistry or by obvious chemical equivalents thereof, for example by a process comprising:

(a) removing at least one protecting group from a protected straight-chain or mono-cyclic polypeptide comprising a hexapeptide residue—as hereinbefore defined, in particular a protected polypeptide having the sequence indicated in formula I, (b) linking together by an amide bond two peptide units, each of which contains at least one amino acid or amino alcohol residue in protected or unprotected form, the peptide units being such that a protected or unprotected straight-chain or mono-cyclic polypeptide comprising a hexapeptide residue—as hereinbefore defined, in particular a protected or unprotected polypeptide having the sequence indicated in formula I, is obtained and, if necessary, carrying out process step (a);

(c) converting a functional group at the N- or C-terminal of a protected or unprotected straight-chain or mono-cyclic polypeptide comprising a hexapeptide residue as hereinbefore defined, in particular the group A or F of a protected or unprotected polypeptide having the sequence indicated in formula I, into another N- or C-terminal functional group, in particular another group A or F, and, if necessary carrying out process step (a);

(d) oxidising a straight chain polypeptide comprising a hexapeptide residue as hereinbefore defined, in particular a polypeptide of formula I wherein $Y_1$ and $Y_2$ are each hydrogen to provide a mono-cyclic polypeptide as hereinbefore defined, in particular a polypeptide of formula I wherein $Y_1$ and $Y_2$ together are a direct bond, and when required converting a polypeptide thus obtained into a salt form or complex thereof.

The above process may for example be carried out analogously to the processes described in the accompanying examples. Insofar as the production of the starting materials is not particularly described, the compounds are known or may be produced and purified in accordance with methods known in the art.

The polypeptides of the invention as well as their pharmaceutically acceptable salts and complexes exhibit valuable pharmacological properties as indicated in animal tests. In particular they exhibit GH-secretion inhibiting activity as indicated e.g. by depression of serum GH-levels in the rat.

This test (TEST I) is carried out employing male rats under Nembutal narcosis. The test-substance is administered at varying, logarithmically staggered doses employing at least 4 rats per dose. The rats are decapitated 15 minutes after administration, the blood is collected and the serum GH-level determined by radio-immunoassay.

Polypeptides in accordance with the invention are active in this test when administered at a dosage in the range of from 0.01 to 100 μg/kg i.v. or i.m.

The said polypeptides, salts and complexes are accordingly useful in the treatment of disorders with an aetiology comprising or associated with excess GH-secretion, e.g. in the treatment of diabetis mellitus and angiopathy as well as of acromegaly.

The said polypeptides, salts and complexes also inhibit gastric- and pancreatic secretion as indicated in standard animal tests e.g. in accordance with the following method for the measurement of the gastric secretion (Test II):

Male rats (220–280 g) are kept in the laboratory in individual cages for several days (14 hours light/day) with 48 hours fasting (but free access to water) immediately prior to the experiment. At start of the experiment the pylorus is ligated under ether anaesthesia and 100 μg/kg pentagastrin are injected s.c. to stimulate gastric secretion. The test compounds are injected simultaneously i.m. 30 mins. later the animals are sacrificed, the volume of gastric juice measured and the acid concentration estimated (titration with thymol blue). The acid output is calculated and the percent inhibition estimated in relation to untreated controls.

Polypeptides in accordance with the invention are active in this test when administered at a dosage in the range of from 0.01 to 100 μg/kg i.m.

The said polypeptides, salts and complexes are thus useful in the treatment of gastro-intestinal disorders, for example in the treatment of gastric ulcer, gastro-intestinal bleeding and acute pancreatitis.

The pharmaceutically acceptable salts and complexes of the polypeptides of the invention show activity of the same order as the free compounds in the above described test methods.

For the above uses the dosage will, of course, vary depending on the compound employed, mode of administration and treatment desired. However, in general satisfactory results are obtained when administered at a daily dosage of from about $20 \times 10^{-9}$ g to about 0.3 mg/kg conveniently given in divided doses 2 to 4 times a day or in sustained release form. For larger mammals, the total daily dosage is in the range of from about 0.002 (e.g. from about 0.07 to about 20 mg polypeptide, and suitable unit dosage forms e.g. for parenteral administration contain from about 0.0005 (e.g. from about 0.02) to about 10 mg, of a polypeptide in accordance with the invention or an equivalent amount of a pharmaceutically acceptable salt of complex thereof, together with a solid or liquid pharmaceutical diluent or carrier therefor.

The daily dosages suitable for any particular compound will of course depend on a number of factors including relative potency of activity. The preferred compound of the invention is the compound of the following example 1, namely

H—(D)-Phe—Cys— Phe— (D)Trp— Lys— Thr— Cys—Thr—ol.

Administered in the form of the acetate, this compound has for example been determined to have an $ID_{50}$ in TEST I above of 0.09 μg/kg i.v. and 0.084 μg/kg i.m., and in TEST II above of 0.7 μg/kg i.m., for gastric juice content and 0.4 μg/kg for acid concentration, the determined $ID_{50}$ being in each case the amount of compound required to effect 50% inhibition for the measured parameter compared with untreated controls. For the known compound somatostatin, determined $ID_{50}$ values are: for TEST I 62 μg/kg i.v. and 5.6 μg/kg i.m. and for TEST II 55 μg/kg for gastric juice content and 35 μg/kg for acid concentration. Thus an indicated daily dosage for the compound of example 1 would be from about $3 \times 10^{-6}$ g to about 0.03 mg/kg for use as GH secretion inhibitor and from about $15 \times 10^{-6}$ g to about 0.15 mg/kg for use as a gastric or pancreatic secretion inhibitor.

In accordance with the foregoing the present invention further provides:

(1) a method of treating disorders with an aetiology comprising or associated with excess GH-secretion (such as diabetes mellitus, angiopathy and acromegaly) as well as of treating gastro-intestinal disorders (such as gastric ulcer, gastro-intestinal bleeding and acute pancreatitis), in a subject in need of such treatment, which method comprises administering to said subject an effective amount of a polypeptide in accordance with the invention or of a pharmaceutically acceptable salt or complex thereof and (2) pharmaceutical compositions comprising a polypeptide in accordance with the invention or of a pharmaceutically acceptable salt or complex thereof, together with a pharmaceutically acceptable diluent or carrier therefor.

In the following examples all temperatures are in °C. and $[\alpha]_D^{20}$-values are uncorrected. The following abbreviations are employed:

---

AcOH = acetic acid
Asp—diol = the asparagine-diol residue

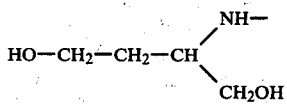

Boc = tert.-butoxycarbonyl
BTFA = boron-tris-trifluoroacetate
DCCI = dicyclohexylcarbodiimide
DMF = N,N—dimethylformamide
HOBT = N—hydroxybenzotriazole
Hy = —NHNH$_2$
Leu—ol = the leucinol residue

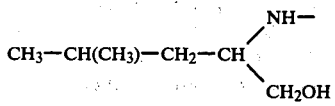

MBzl = p-methoxybenzyl
Me = methyl
MeOH = methanol
MePhe = —(N—methyl)—Phe—
NEt$_3$ = triethylamine
ONP = 4-Nitrophenoxy
Phe(pF) = -p-F—Phe—

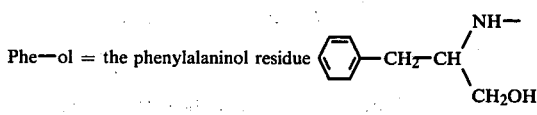

Ser—ol = the serinol residue —NH—CH(CH$_2$OH)$_2$
TFA = trifluoroacetic acid
THF = tetrahydrofuran

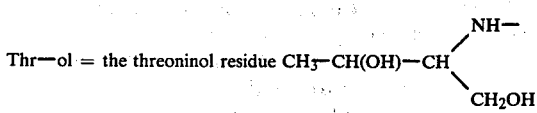

Z = benzyloxycarbonyl

---

EXAMPLE 1A

H—(D)-Phe—Cys— Phe— (D)Trp— Lys— Thr— Cys—Thr—ol.

0,70 g Boc—(D)Phe—Cys(MBzl)—Phe—(D)Trp—Lys(Boc)—Thr—Cys—(MBzl)—Thr—ol and 6.0 ml of thioanisol are dissolved in 9 ml TFA at 0°. The solution is cooled to −10° and 12 ml ca. 2 M BTFA in TFA are added with stirring. Stirring is continued for 1½ hours at −5° to −10° and 50 ml cold abs.MeOH (−70°) are added. After a further 5 min. 1 liter abs. ether and 5 ml ca. 5 N HCl in ether are added with stirring. The precipitated product is filtered off, washed briefly with ether and the residue dissolved immediately in 2.5 l dioxan/H$_2$O (7:3). The pH is adjusted to pH 7-7.5 by the addition of dilute ammonia solution. The mixture is stirred in an open vessel at room temperature until it tests negative for —SH groups (e.g. Ellmann-Test). The pH is adjusted to 3–4 by addition of HCl and the obtained solution concentrated under vacuum, and the product lyophilised. The lyophilisate is dissolved in a small quantity 10% AcOH and purified by gel-chromatography (Bio-Rad P4) using 10% AcOH. Fractions containing the desired product are collected and lyophilised, to yield the title compound: $[\alpha]_D^{20} = -42°$ (c=0.5 in 95% AcOH).

The starting material may be obtained as follows:

(a) Z—Lys(Boc)—Thr—OMe 13.5 ml chloroformic acid isobutyl ester are added with stirring to 56 g Z—Lys(Boc)—OH in the form of the dicyclohexylamine salt dissolved in 1200 ml THF, pre-cooled to −20°. Stirring is continued for a further 20 minutes at −15° C. and a cold solution (−21°) of 21 g HCl.H—THr—OMe in 600 ml THF is then added. 17 ml triethylamine are added drop-wise at −15° C., the reaction mixture stirred for 18 hours at 0° and the product subjected to strong concentration under vacuum. Dilution is effected with ether/ethylacetate (1:1) and the precipitated dicyclohexylamine salt filtered off. The filtrate is washed out with H$_2$O, 2 N citric acid, 10% KHCO$_3$ and H$_2$O. The organic phase is dried over Na$_2$SO$_4$ and evaporated to dryness, to yield the title compound as a resin: $[\alpha]_D^{20} = -14°$ (c=1 in DMF).

(b) Z—Phe—(D)Trp—OH 9.0 g Z-Phe-OH in 150 ml acetonitrile are cooled to −18° and 3.4 ml N-methyl-morpholine followed by 4.1 ml chloroformic acid isobutyl ester are added. The solution is stirred for 15 minutes at −15° and a cold solution of 6.2 g H—(D)Trp—OH in 30 ml 1 N NaOH and 100 ml acetonitrile is added, and stirring continues for a further 18 hours at −5° to 0°. The reaction mixture is concentrated under vacuum, diluted with water and extracted 3× with a small quantity of ether. The aequeous phase is adjusted to ca. pH2 by the addition of 4 N H$_2$SO$_4$ and the precipitate extracted with ether/acetic acid. The organic phase is washed with water and dried over Na$_2$SO$_4$. After evaporation under vacuum, the residue is crystallized from ether/petrolether to yield the title compound: m.p. 113° C., $[\alpha]_D^{20} = -5°$ (c=0.9 in DMF).

(c) Z—Phe—(D)Trp—Lys(Boc)—Thr—OMe 6,0 g Z—Lys(Boc)—Thr—OMe in 150 ml MeOH are hydrogenated in the presence of Pd/C. The product is filtered, washed with MeOH and the filtrate evaporated under vacuum. The residue is dissolved together with 4.8 g Z—Phe—(D)Trp—OH and 2.0 g HOBT in 50 ml DMF. The solution is cooled to −15° and 2.1 g DCCI in 15 ml DMF are added with stirring. The solution is stirred for a further 2 days at 0°, evaporated under vacuum, diluted with acetic acid/ether (1:1) and the precipitate dicyclohexylurea filtered off. The filtrate is washed with 2 N citric acid, 10% KHCO$_3$ and H$_2$O. The organic phase is dried over Na$_2$SO$_4$ and evaporated. The residue is chromatographed over silica-gel with CH$_2$Cl$_2$/MeOH as eluant. The fractions containing the desired product are collected and evaporated under vacuum to yield the title compound: $[\alpha]_D^{20} = -7°$ (c=0.9 in DMF).

(d) H—Phe—(D)Trp—Lys(Boc)—Thr—OMe 1.2 g Z—Phe—(D)Trp—Lys(Boc)—Thr—OMe in 50 ml MeOH are hydrogenated in the presence of 10% Pd/C and the solution filtered and evaporated under vacuum to yield the title compound as a foam: $[\alpha]_D^{20} = -18°$ (c=1 in MeOH).

(e) Boc—(D)Phe—Cys(MBzl)—OH 8.4 ml NEt$_3$ followed by 8.3 ml chloroformic acid isobutyl ester are added to 16 g Boc—(D)Phe—OH in 300 ml THF pre-cooled to $-20°$. The obtained mixture is stirred for 10 minutes at $-15°$ and a cold solution of H—Cys—(MBzl)—OH and 11.5 ml NEt$_3$ in 400 ml THF/H$_2$O (5:1) are subsequently added drop-wise. The reaction mixture is stirred for ca. 2 days at 0°, concentrated under vacuum, diluted with 1.3 l H$_2$O and extracted with ether. The aequeous phase is adjusted to pH 2.0 by the addition of 4 N H$_2$SO$_4$ and the precipitate extracted with ethyl acetate. The ethyl acetate extract is washed with water, dried over Na$_2$SO$_4$ and evaporated under vacuum. The residue is purified by chromatography over silica gel with ether/1% AcOH as eluant. The fractions containing the desired product are combined and evaporated under vacuum to yield the title compound: $[\alpha]_D^{20} = -18°$ (c=1.1 in DMF).

(f) Boc—(D)Phe—Cys(MBzl)—Phe—(D)Trp—Lys(Boc)—Thr—OMe 0.30 g DCCI are added with stirring to 0.67 g Boc—(D)Phe—Cys(MBzl)—OH, 1.0 g H—Phe—(D)Trp—Lys(Boc)—Thr—OMe and 0.5 g HOBT dissolved in 30 ml DMF, pre-cooled to $-20°$. The reaction mixture is stirred for ca. 12 hours at from $-5°$ to 0° and for ca. 4 hours at room temperature. The precipitated dicyclohexyl urea is filtered off and the filtrate washed with 2 N citric acid, 10% KHCO$_3$ and H$_2$O. The organic phase is dried over Na$_2$SO$_4$ purified and concentrated. The product is precipitated by the addition of ether, filtered and dried to yield the title compound: m.p. 160°, $[\alpha]_D^{20} = -30°$ (c=1 in MeOH).

(g) Boc—(D)Phe—Cys(MBzl)—Phe—(D)Trp—Lys(Boc)—Thr—NHNH$_2$ 1.5 ml hydrazine hydrate are added to 0.9 g Boc—(D)Phe—Cys—(MBzl)—Phe—(D)Trp—Lys(Boc)—Thr—OMe dissolved in 15 ml DMF. The solution is allowed to stand for 5 hours at room temperature and aequeous MeOH is added. The precipitate is filtered off, washed with MeOH/H$_2$O (1:9) and dried to yield the title compound: m.p. 160°, $[\alpha]_D^{20} = -19°$ (c=1 in DMF).

(h) H—Cys(MBzl)—Thr—ol trifluoroacetate

A solution of 7.1 g Boc—Cys(MBzl)—Thr—ol and 5 ml thioanisole in 25 ml methylenechloride are added to 50 ml TFA and allowed to stand for 20 minutes at room temperature. The solution is diluted with ca. 1.5 l ether and the precipitate filtered off, washed with ether and dried to yield the title compound: $[\alpha]_D^{20} = 8.3°$ (c=1.1 in 95% AcOH).

(i) Boc—Cys(MBzl)—Thr—ol 2.1 ml N-methylmorpholine are added with stirring to 6.3 g Boc—Cys(MBzl)—OH in 50 ml THF pre-cooled to $-20°$, followed by the drop-wise addition at $-15°$ of 2.4 ml chloroformic acid isobutyl ester. After stirring for 5 minutes at $-15°$ a cold solution ($-10°$) comprising 3.3 g H—Thr—ol hydrochloride and 4.1 ml N-methylmorpholine in 30 ml DMF are added. The mixture is stirred for 2 hours at 0° and for a further 2 hours at room temperature. 50 ml 10% KHCO$_3$ are added, the reaction mixture concentrated under vacuum, diluted with ethyl acetate and washed 3× with 2 N citric acid, 3× with 10% KHCO$_3$ and subsequently with 30% NaCl solution. The organic phase is dried over Na$_2$SO$_4$ and evaporated under vacuum to yield the title compound as an oil: $[\alpha]_D^{20} = -31°$ (c=1.3 in DMF).

(j) Boc—(D)Phe—Cys(MBzl)—Phe—(D)Trp—Lys(Boc)—Thr—Cys(MBzl)—Thr—ol 0.7 ml ca. 5 N HCl in ether are added with stirring to 0.82 g Boc—(D)Phe—Cys(MBzl)—Phe—(D)Trp—Lys(Boc)—Thr—NH—NH$_2$ in 30 ml DMF pre-cooled to $-20°$, followed by, in toto, 0.8 ml, 10% tert-.butylnitrite in DMF. The mixture is stirred for 15 minutes at $-20°$ to $-15°$. 0.56 ml NEt$_3$ are added at $-25°$ C., followed by a solution of 0.51 g H—Cys(MBzl)—Thr—ol hydrochloride in 3 ml DMF, pre-cooled to $-15°$, and the whole is stirred for 20 hours at $-5°$ to 0° and for a further 3 hours at room temperature. The reaction mixture is diluted with ca. 100 ml methanol and the product precipitated by addition of ca. 40 ml H$_2$O. The precipitated is filtered off, washed with aequeous MeOH and dried to yield the title compound: decomposition at 170°, $[\alpha]_D^{20} = -20°$ (c=1 in DMF).

Example 1B

The product of example 1A may also be prepared in accordance with the following synthetic sequences:

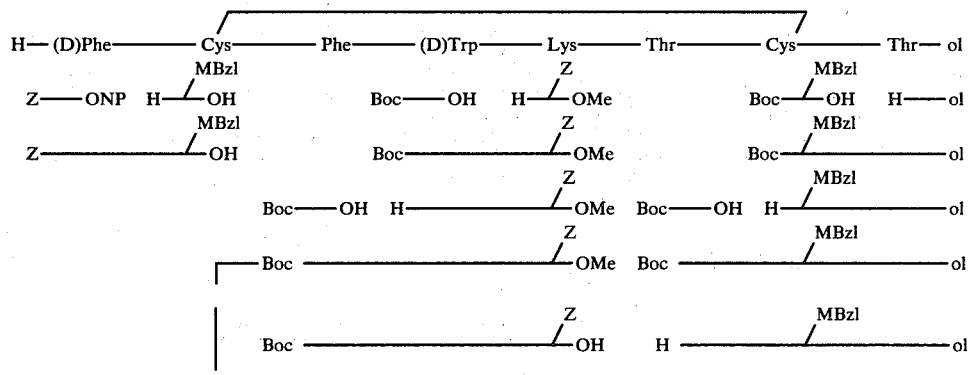

Example 1B-continued

The product of example 1A may also be prepared in accordance with the following synthetic sequences:

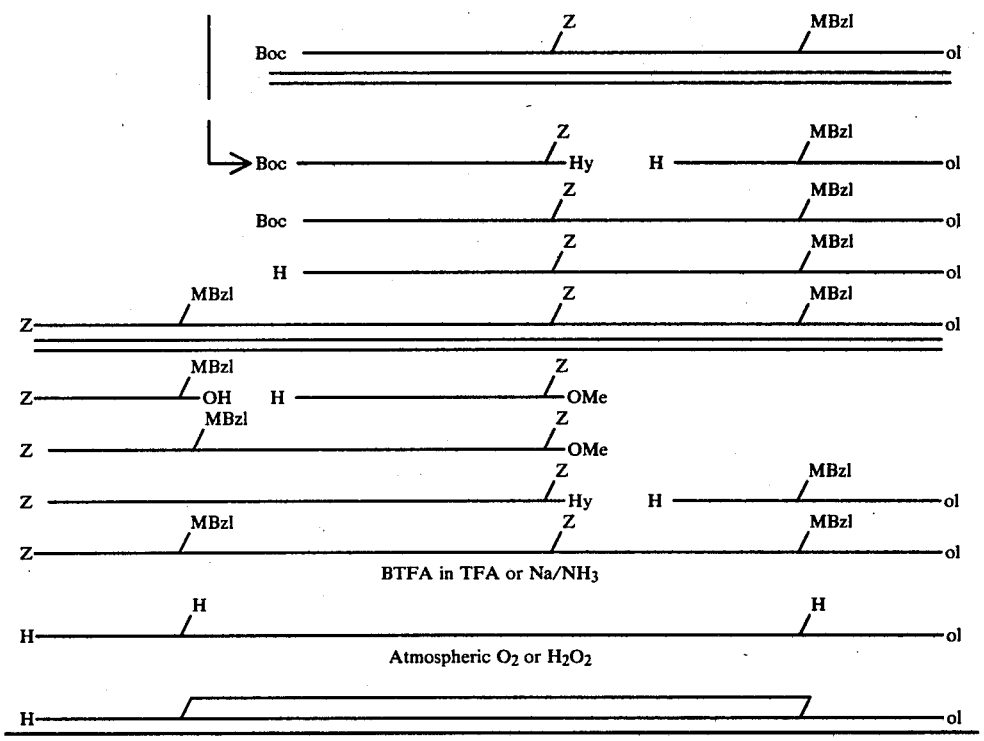

The following compounds may be produced analogously to the above described processes (all compounds as acetate unless otherwise indicated):

EXAMPLE 19

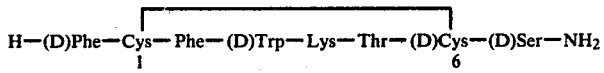

H—(D)Phe—Cys—Phe—(D)Trp—Lys—Thr—(D)Cys—(D)Ser—NH$_2$
        1                                    6

HCl salt: $[\alpha]_D^{20}$ in 95% AcOH = $-85°$ (c=0.4).

EXAMPLE 20

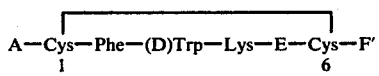

A—Cys—Phe—(D)Trp—Lys—E—Cys—F'
   1                    6

| Example No. | A | E | F' | $[\alpha]_D^{20}$ in 95% AcOH |
|---|---|---|---|---|
| 2 | H | —Thr— | —NH$_2$ | +33° (c = 1.1) |
| 3 | H—(D)Phe— | —Thr— | —(D)Ser—NH$_2$ | −48° (c = 1.0) |
| 4 | H—(D)Phe— | —Thr— | —NH$_2$ | −35° (c = 1.0) |
| 5 | H—(D)Phe— | —Thr— | —Phe—ol | −41° (c = 1.0) |
| 6 | H—(D)Phe— | —Thr— | —Leu—ol | −41° (c = 1.0) |
| 7 | H—(D)Phe— | —Thr— | —Asp—diol | −42° (c = 1.0) |
| 8 | H—Nle— | —Thr— | —(D)Ser—NH$_2$ | −42° (c = 1.0) |
| 9 | H | —Thr— | —(D)Ser—NH$_2$ | +26° (c = 0.5) |
| 10 | H—(D)Phe— | —(D)Ala— | —(D)Ser—NH$_2$ | −23° (c = 0.9) |
| 11 | H—Asn— | —Thr— | —(D)Ser—NH$_2$ | −28° (c = 0.5) |
| 12 | H—(D)MePhe— | —Thr— | —THr—ol | −63° (c = 1.0) |
| 13 | H—Nle—Asn— | —Thr— | —Thr—ol | −40° (c = 1.0) |
| 14 | H—(D)Phe— | —(D)Ala— | —Thr—ol | −9° (c = 1.0) |
| 15 | H—(D)Phe— | —Thr— | —Ser—ol | −43° (c = 1.1) |
| 16 | H—(D)Phe— | —(D)Thr— | —Thr—ol | −73° (c = 1.0) |
| 17 | ⌬—(CH$_2$)$_2$—CO— | —Thr— | —Thr—ol | −25° (c = 0.9) |
| 18 | H—(D)Phe(pF)— | —Thr— | —Thr—ol | −41° (c = 0.5) |

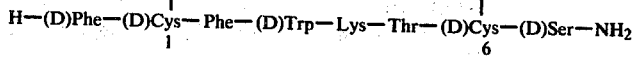

$[\alpha]_D^{20}$ in 95% AcOH = −102° (c=1.0).

EXAMPLE 21

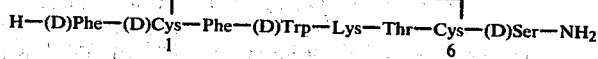

$[\alpha]_D^{20}$ in 95% A—OH = −30° (c=1.0).

EXAMPLE 22

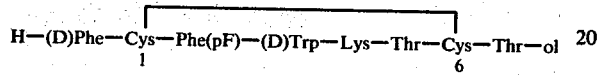

$[\alpha]_D^{20}$ in 95% AcOH = −42° (c=1.0)

EXAMPLE 23

Proceeding analogously to examples 1 through 22, but omitting the final oxidisation step, the straight-chain polypeptides corresponding to each of the individual monocyclic polypeptides recited (i.e. wherein the —Cys— residues in the 1- and 6-positions are not linked) are produced. Thus omitting the final oxidisation step from the process of example 1A there is produced the straight-chain polypeptide of formula:

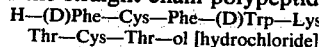

$[\alpha]_D^{20}$ in 95% AcOH = −35° (c=0.5).

We claim:

1. A polypeptide of formula (I)

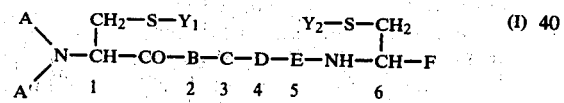

wherein

A is $C_{1-12}$ alkyl, $C_{7-10}$ phenylalkyl or a group of formula RCO—, whereby
 (i) R is hydrogen, $C_{1-11}$ alkyl, phenyl or $C_{7-10}$ phenylalkyl, or
 (ii) RCO— is
  (a) an L- or D-phenylalanine residue optionally ring-substituted by halogen, $NO_2$, $NH_2$, OH, $C_{1-3}$ alkyl and/or $C_{1-3}$ alkoxy
  (b) —Asn— or the residue of a natural α-amino acid having a hydrocarbyl side chain other than defined under (a) above or of a corresponding D-amino acid, or
  (c) a dipeptide residue in which the individual amino acid residues are the same or different and are selected from those defined under (a) and/or (b) above, the α-amino group of amino acid residues (a) and (b) and the N-terminal amino group of dipeptide residues (c) being optionally mono- or di-$C_{1-12}$ alkylated, A' is hydrogen or, when A is $C_{1-12}$ alkyl or $C_{7-10}$ phenylalkyl, also $C_{1-12}$ alkyl or $C_{7-10}$ phenylalkyl, B is —Phe— optionally ring-substituted by halogen, $NO_2$, $NH_2$, OH, $C_{1-3}$ alkyl and/or $C_{1-3}$ alkoxy, C is —(L)— or —(D)—Trp— optionally α-N-methylated and optionally benzene-ring-substituted by halogen, $NO_2$, $NH_2$, OH, $C_{1-3}$ alkyl and/or $C_{1-3}$ alkoxy, D is —Lys— optionally α-N-methylated and optionally ε-N-$C_{1-3}$ alkylated, E is —Thr— or —Ala— each in (D)- or (L)- form and each being optionally α-N-methylated, F is a group of formula

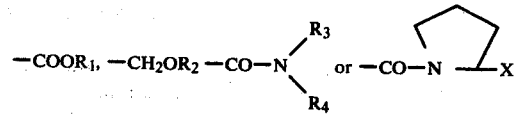

wherein $R_1$ is hydrogen or $C_{1-3}$ alkyl, $R_2$ is hydrogen or the residue of a physiologically acceptable, physiologically hydrolysable ester, $R_3$ is hydrogen, $C_{1-3}$ alkyl, phenyl, benzyl or $C_{9-10}$ phenylalkyl, $R_4$ is hydrogen, $C_{1-3}$ alkyl or, when $R_3$ is hydrogen or methyl, also a group of formula —CH($R_5$)—X wherein $R_5$ is hydrogen, —$(CH_2)_2$—OH, —$(CH_2)_3$—OH, —$CH_2$—OH, —CH($CH_3$)—OH, isobutyl or benzyl and X is a group of formula

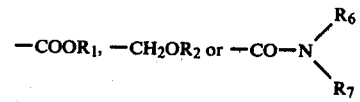

wherein $R_1$ and $R_2$ have the meanings given above, $R_6$ is hydrogen or $C_{1-3}$ alkyl and $R_7$ is hydrogen, $C_{1-3}$ alkyl, phenyl or $C_{7-10}$ phenylalkyl, the group —CH($R_5$)—X having the D- or L-configuration, and $Y_1$ and $Y_2$ are each hydrogen or together represent a direct bond, whereby the residues in the 1- and 6-position each independently have the L- or D-configuration, with the proviso (i) that D- and/or L-cysteine residues are present at the 1- and 6-positions only, and
(ii) that when $R_5$ is benzyl, X is a group of formula

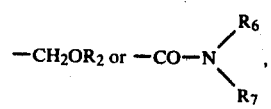

or a group of formula —COOR$_1$, wherein R$_1$ is C$_{1-3}$ alkyl, or a pharmaceutically acceptable acid addition salt or complex thereof.

2. A compound according to claim 1, wherein R$_3$ is hydrogen, C$_{1-3}$alkyl or phenyl.

3. A compound according to claim 1, wherein, when R$_5$ is benzyl, X is a group of formula

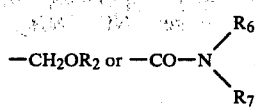

4. A compound according to claim 1, wherein
R$_3$ is hydrogen or methyl and
R$_4$ is a group of formula —CH(R$_5$)—X.

5. A compound according to claim 3, wherein
R$_3$ is hydrogen or methyl and
R$_4$ is a group of formula —CH(R$_5$)—X.

6. A compound according to claim 1, wherein
A is a group of formula RCO—, whereby
  (i) R is C$_{1-11}$alkyl or C$_{7-10}$phenylalkyl, or
  (ii) RCO— is
     (a) an L- or D-N-(C$_{1-8}$alkyl)-phenylalanine residue, or
     (b) a leucine or nor-leucine residue, said residues having the L- or D-configuration,
A' is hydrogen, and
F is a group of formula

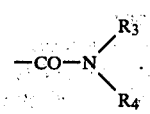

7. A compound according to claim 6, wherein
F is a group of formula

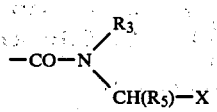

wherein
R$_3$ is hydrogen or methyl,
R$_5$ is —CH$_2$OH, —CH(CH$_3$)—OH, isobutyl, benzyl —(CH$_2$)$_2$—OH or —(CH$_2$)$_3$—OH, and
X is a group of formula

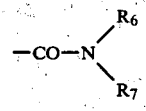

or a group of formula —CH$_2$—OR$_2$, wherein R$_2$ is hydrogen, HCO, C$_{2-12}$alkylcarbonyl, C$_{8-12}$ phenylalkylcarbonyl or benzoyl.

8. A compound according to claim 1, wherein
B is —Phe—,
C is —(D)Trp—,
D is —Lys—, —MeLys— or —Lys(ε—Me)—, and
E is —Thr—.

9. A compound according to claim 6, wherein
B is —Phe—,
C is —(D)Trp—,
D is —Lys—, —MeLys— or —Lys(ε—Me)—, and
E is —Thr—.

10. A compound according to claim 1, wherein X is a group of formula —CH$_2$OR$_2$.

11. A compound according to claim 7, wherein X is a group of formula —CH$_2$OR$_2$.

12. A polypeptide according to claim 1, wherein
A is C$_{1-3}$ alkyl, C$_{7-10}$ phenylalkyl or a group of formula RCO—,
A' is hydrogen,
R is hydrogen, C$_{1-3}$ alkyl, phenyl or C$_{7-10}$ phenylalkyl or
RCO is
  (a) an L- or D-phenylalanine residue optionally mono-ring-substituted by halogen, NO$_2$, NH$_2$, OH, C$_{1-3}$ alkyl or C$_{1-3}$ alkoxy, or
  (b) the residue of a natural α-amino acid having a hydrocarbyl side chain other than defined under (a) above or of a corresponding D-amino acid, the amino group of amino acid residues (a) and (b) being optionally mono-C$_{1-3}$ alkylated,
F is a group of formula

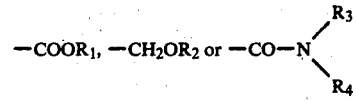

R$_2$ is hydrogen,
R$_3$ is hydrogen or C$_{1-3}$ alkyl,
R$_7$ is hydrogen or C$_{1-3}$ alkyl and
Y$_1$ and Y$_2$ together represent a direct bond,
and B, C, D, E, R$_1$, R$_4$, R$_5$, R$_6$ and X have the meanings given above in claim 1, as well as the acid addition salts and complexes thereof.

13. A polypeptide according to claim 1 of formula

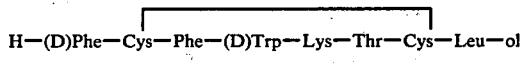

or a salt form or a complex thereof.

14. A polypeptide according to claim 1 of formula

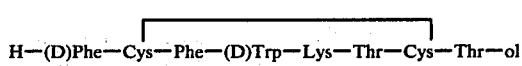

or a salt form or a complex thereof.

15. A compound according to claim 1 selected from the group consisting of

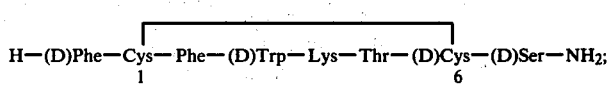 (q)

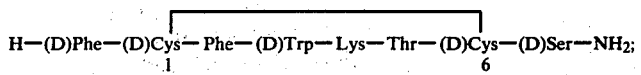 (r)

-continued (s)
H—(D)Phe—(D)Cys—Phe—(D)Trp—Lys—Thr—Cys—(D)Ser—NH$_2$;
　　　　　　1　　　　　　　　　　　　　　　6

(t)
H—(D)Phe—Cys—Phe(pF)—(D)Trp—Lys—Thr—Cys—Thr—ol; and
　　　　　1　　　　　　　　　　　　　　　6

(u) H—(D)Phe—Cys—Phe—(D)Trp—Lys—Thr—Cys—Thr—ol or a pharmaceutically acceptable acid addition salt or complex thereof.

16. A compound according to claim 1 of the formula $$\begin{array}{c} CH_2-S-Y_1 \\ | \\ A-NH-CH-CO-B-(D)Trp-Lys-E-NH-CH-F \\ 1 \hspace{4cm} 6 \end{array} \quad \begin{array}{c} Y_2-S-CH_2 \\ | \\ \end{array}$$

wherein
A is RCO— and
R is $C_{7-10}$ phenalkyl or
RCO is H—(D)Phe— or H—(D)MePhe—, optionally ring substituted by halo; H—Nle—, H—Asn— or H—Nle—Asn—;
B is Phe, optionally ring substituted by halo;
E is —Thr—, —(D)Thr— or —(D)Ala—; and
F is $$-CONH_2 \text{ or } -CON\begin{array}{c} R_3 \\ \diagdown \\ \diagup \\ CH(R_5)-X \end{array}$$

where
R$_3$ is hydrogen;
R$_5$ is —(CH$_2$)$_2$—OH, —CH$_2$—OH, —CH(CH$_3$)—OH, isobutyl or benzyl; and
X is —CONH$_2$ or —CH$_2$OR$_2$
where
R$_2$ is hydrogen or a physiologically acceptable, physiologically hydrolysable ester thereof and
Y$_1$ and Y$_2$ are each hydrogen or together are a direct bond,
wherein the amino acid residues represented by F and in the 1- and 6-position each independently have the L- or D-configuration or
a pharmaceutically acceptable acid addition salt or complex thereof.

17. A compound according to claim 1 having the structure

A—Cys—Phe—(D)Trp—Lys—E—Cys—F selected from the group in which A, E and F are respectively
(a) H—(D)Phe—, —Thr—, and —(D)Ser—NH$_2$;
(b) H—(D)Phe—, —Thr—, and —NH$_2$;
(c) H—(D)Phe—, —Thr—, and —Phe—ol;
(d) H—(D)Phe—, —Thr—, and —Asp—diol;
(e) H—Nle—, —Thr—, and —(D)Ser—NH$_2$;
(f) H—(D)Phe—, —(D)Ala—, and —(D)Ser—NH$_2$;
(g) H—Asn—, —Thr—, and —(D)Ser—NH$_2$;
(h) H—(D)MePhe—, —Thr—, and —Thr—ol;
(i) H—Nle—Asn—, —Thr—, and —Thr—ol;
(j) H—(D)Phe—, —(D)Ala—, and —Thr—ol;
(k) H—(D)Phe—, —Thr—, and —Ser—ol;
(l) H—(D)Phe—, —(D)Thr—, and —Thr—ol;

(m)
⟨phenyl⟩—(CH$_2$)$_2$—CO—, —Thr—, and —Thr—ol;

(n) H—(D)Phe(pF)—, —Thr—, and —Thr—ol;
or a pharmaceutically acceptable acid addition salt or complex thereof.

18. A compound according to claim 1 in which E is —(L) or —(D)Thr— or —(D)Ala—.

19. A method of treating disorders with an aetiology comprising or associated with excess GH-secretion in a subject in need of such treatment, which method comprises administering to said subject an effective amount of a polypeptide as claimed in claim 1 or of a pharmaceutically acceptable salt form or complex thereof.

20. A method of treating gastro-intestinal disorders in a subject in need of such treatment, which method comprises administering to said subject an effective amount of a polypeptide as claimed in claim 1 or of a pharmaceutically acceptable salt form or complex thereof.

21. A pharmaceutical composition useful in the treatment of excess GH-secretion or gastro-intestinal disorders comprising a polypeptide as claimed in claim 1 or a pharmaceutically acceptable salt form or complex thereof together with a pharmaceutically acceptable diluent or carrier therefor.

* * * * *

UNITED STATES PATENT AND TRADEMARK OFFICE

CERTIFICATE EXTENDING PATENT TERM
UNDER 35 U.S.C. 156

Patent No.     : 4,395,403

Dated          : July 26, 1983

Inventor(s)    : WILFRIED BAUER ET AL

Patent Owner   : SANDOZ, LTD.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

I have caused the seal of the Patent and Trademark Office to be affixed this <u>11th</u> day of <u>December 1989</u>.

Jeffrey M. Samuels
Acting Commissioner of
   Patents and Trademarks